United States Patent
Zeng et al.

(10) Patent No.: US 11,389,780 B2
(45) Date of Patent: Jul. 19, 2022

(54) REACTION SYSTEM, CATALYST AND METHOD FOR PREPARING β-PHENYLETHANOL

(71) Applicant: WANHUA CHEMICAL GROUP CO., LTD., Shandong (CN)

(72) Inventors: Wei Zeng, Shandong (CN); Changsheng Chen, Shandong (CN); Yuan Li, Shandong (CN); Zaigang Yang, Shandong (CN); Hengdong Yang, Shandong (CN); Jianglin Hu, Shandong (CN); Yunhai Liu, Shandong (CN); Ke Ding, Shandong (CN); Yuanye Bao, Shandong (CN)

(73) Assignee: WANHUA CHEMICAL GROUP CO., LTD., Shandong (CN)

( * ) Notice: Subject to any disclaimer, the term of this patent is extended or adjusted under 35 U.S.C. 154(b) by 466 days.

(21) Appl. No.: 16/475,839

(22) PCT Filed: Mar. 14, 2017

(86) PCT No.: PCT/CN2017/076663
§ 371 (c)(1),
(2) Date: Nov. 1, 2019

(87) PCT Pub. No.: WO2018/126531
PCT Pub. Date: Jul. 12, 2018

(65) Prior Publication Data
US 2020/0298198 A1    Sep. 24, 2020

(30) Foreign Application Priority Data
Jan. 3, 2017  (CN) .......................... 201710000984.7

(51) Int. Cl.
*B01J 19/00*    (2006.01)
*B01J 19/08*    (2006.01)
(Continued)

(52) U.S. Cl.
CPC .......... *B01J 19/0093* (2013.01); *B01J 19/10* (2013.01); *B01J 23/72* (2013.01); *B01J 23/755* (2013.01);
(Continued)

(58) Field of Classification Search
CPC ...... B01J 19/00; B01J 19/006; B01J 19/0093; B01J 19/08; B01J 19/10; B01J 19/24;
(Continued)

(56) References Cited

U.S. PATENT DOCUMENTS 2,524,096 A    10/1950  Wood et al.
2,822,403 A     2/1958  Hopff et al.
(Continued)

FOREIGN PATENT DOCUMENTS

CN    1111169 A    11/1995
CN    1827218 A     9/2006
(Continued)

OTHER PUBLICATIONS

Machine translation of the abstract of CN 101450300 A, was publish Jun. 10, 2009 (Year: 2009).*
EP Partial Search Report for EP 17889831.8 dated Jul. 28, 2020.

*Primary Examiner* — Natasha E Young
(74) *Attorney, Agent, or Firm* — Stinson LLP

(57) ABSTRACT

Disclosed is a method for preparing β-phenylethanol. The method comprises the following steps: (1) reducing a catalyst in a reactor in advance; (2) introducing pre-heated hydrogen gas to warm the reactor to a predetermined temperature; and (3) introducing a raw material styrene oxide to perform a hydrogenation reaction so as to obtain the β-phenylethanol. The catalyst is Ni—Cu/Al$_2$O$_3$ nanosized self-assembled catalyst. The reactor is an ultrasonic field micro- (Continued)

packed bed reactor. The method of the present invention enables the selectivity of the β-phenylethanol to reach 99% or more.

20 Claims, 4 Drawing Sheets

(51) Int. Cl.
*B01J 19/10* (2006.01)
*B01J 19/24* (2006.01)
*B01J 23/72* (2006.01)
*B01J 23/755* (2006.01)
*B01J 35/10* (2006.01)
*B01J 37/04* (2006.01)
*B01J 37/06* (2006.01)
*C07C 29/156* (2006.01)
*B01J 37/00* (2006.01)
*B01J 21/04* (2006.01)
*C07C 33/22* (2006.01)

(52) U.S. Cl.
CPC ........... *B01J 37/0045* (2013.01); *B01J 37/04* (2013.01); *B01J 37/06* (2013.01); *C07C 29/156* (2013.01); *B01J 21/04* (2013.01); *B01J 2219/0086* (2013.01); *B01J 2219/00795* (2013.01); *B01J 2219/00891* (2013.01); *B01J 2219/00909* (2013.01); *B01J 2219/00932* (2013.01); *C07C 33/22* (2013.01)

(58) Field of Classification Search
CPC ... B01J 21/00; B01J 21/02; B01J 21/04; B01J 23/00; B01J 23/70; B01J 23/72; B01J 23/74; B01J 23/755; B01J 35/00; B01J 35/02; B01J 35/10; B01J 35/1052; B01J 35/1061; B01J 35/1066; B01J 2219/00; B01J 2219/00781; B01J 2219/00788; B01J 2219/00792; B01J 2219/00795; B01J 2219/00819; B01J 2219/00835; B01J 2219/00851; B01J 2219/00858; B01J 2219/0086; B01J 2219/00864; B01J 2219/00873; B01J 2219/00891; B01J 2219/00905; B01J 2219/00909; B01J 2219/00925; B01J 2219/00932; C07C 29/00; C07C 29/132; C07C 29/136; C07C 29/14; C07C 29/141; C07C 29/15; C07C 29/151; C07C 29/153; C07C 29/156; C07C 33/00; C07C 33/18; C07C 33/20; C07C 33/22

See application file for complete search history.

(56) References Cited

U.S. PATENT DOCUMENTS

| | | | |
|---|---|---|---|
| 4,064,186 | A | 12/1977 | Gibson et al. |
| 4,943,667 | A | 7/1990 | Hoelderich et al. |
| 6,166,269 | A | 12/2000 | Chaudhari et al. |
| 6,979,753 | B2 | 12/2005 | Rode et al. |
| 7,819,967 | B2 * | 10/2010 | Kyota ................ C09B 67/0091 106/497 |
| 2005/0131258 | A1 | 6/2005 | Rode et al. |
| 2007/0071664 | A1 | 3/2007 | Bellos |
| 2016/0129424 | A1 * | 5/2016 | Pant ........................ B01J 37/18 502/343 |

FOREIGN PATENT DOCUMENTS

| | | | |
|---|---|---|---|
| CN | 101041623 | A | 9/2007 |
| CN | 101450300 | A * | 6/2009 |
| CN | 101890372 | A | 11/2010 |
| CN | 202898377 | U | 4/2013 |
| CN | 104162395 | A | 11/2014 |
| JP | 1-233246 | | 9/1989 |
| WO | 2005063372 | A2 | 7/2005 |
| WO | 2016156841 | A1 | 10/2016 |

* cited by examiner

REACTION SYSTEM, CATALYST AND METHOD FOR PREPARING β-PHENYLETHANOL

CROSS-REFERENCE TO RELATED APPLICATION

The present application is a national phase application of International Application No. PCT/CN2017/076663 (published as WO 2018/126531), filed Mar. 14, 2017, which claims priority to Chinese Application No. 201710000984.7, filed Jan. 3, 2017, both of which are hereby incorporated by reference in their entireties.

TECHNICAL FIELD

The present invention relates to a reaction system for preparing β-phenylethanol, a catalyst used, a preparation method of the catalyst and a method for preparing β-phenylethanol, and in particular to a method for preparing β-phenylethanol by hydrogenation using styrene oxide as a raw material.

BACKGROUND ART

β-phenylethanol (PEA), also known as 2-phenylethanol, phenylethanol and beta-phenylethanol, is a simple aromatic primary alcohol. It is a colorless liquid at room temperature, with a light, delicate and long-lasting rose aroma. It was first discovered as a characteristic aroma compound in plant flowers, and naturally existed in aromatic oils such as neroli, rose oil and geranium oil.

β-phenylethanol is widely used in various food flavors and tobacco flavors because of its soft, pleasant and long-lasting rose aroma. It is a main raw material for the preparation of rose-flavored food additives and rose-flavored flavors. The usage amount of β-phenylethanol as a fragrance on a global scale is second only to vanillin. At the same time, due to that β-phenylethanol is stable in alkali condition and insoluble in water, it is often used in lotions and soaps. In addition, since β-phenylethanol has good antibacterial efficacy, it can also be used in eyedrops and skin care products.

At present, β-phenylethanol on the market is basically chemically synthesized. The main chemical synthesis methods for β-phenylethanol are the benzene-oxirane method (Friedel-Crafts reaction) and the styrene oxide (STO) hydrogenation method. In the international market, benzene-oxirane products account for about 40%, and styrene oxide hydrogenation products account for about 60%. The products produced by the benzene-oxirane method contain different trace impurities, and the aroma varies greatly, and the quality has not yet reached the standard of the fragrance. Therefore, the styrene oxide hydrogenation method is mainly employed in the fragrance industry.

For the preparation of β-phenylethanol by hydrogenation of styrene oxide, both homogeneous and heterogeneous methods have been reported in the literatures. The homogeneous method is hardly used in actual production due to problems such as difficulty in catalyst recovery and difficulty in product separation. Most patent documents are devoted to the research and development of heterogeneous catalytic processes. In the heterogeneous catalytic process, how to improve the selectivity of β-phenylethanol and the life of the catalyst have always been hot spots and difficult points. The key to improve the selectivity of β-phenylethanol is to ensure good effect of hydrogen mass transfer. U.S. Pat. No. 3,579,593 describes a method for preparing β-phenylethanol by using skeletal Ni and Pd as catalysts, and the comparative examples show that when Ni alone is used as a catalyst, the by-product ethylbenzene content is as high as 11%; when Pd alone is used as a catalyst, it will produce about 10% phenylacetaldehyde; the yields of β-phenylethanol are all low, only about 85%; meanwhile, if the reaction solution contains a large amount of phenylacetaldehyde, phenylacetaldehyde will further react with the product β-phenylethanol to produce high-boiling substances that block the catalyst pores and cause catalyst deactivation. U.S. Pat. Nos. 6,166,269 and 4,064,186 propose the addition of auxiliary agents such as NaOH, $Na_2CO_3$, KOH and the like to the reaction system. Although the selectivity and yield of β-phenylethanol are greatly improved, the addition of the auxiliary alkali shortens the life of the catalyst and causes many difficulties such as difficulty in separating the later products, easily blocking towers. U.S. Pat. No. 2,822,403 proposes to prepare β-phenylethanol under alkaline conditions using water as a solvent, Raney Ni or Co as a catalyst; However, this process requires a large amount of water, and at the same time an emulsifier is required to be added to adjust the compatibility of water and styrene oxide, which brings a great difficulty for the separation of later products. At present, styrene oxide hydrogenation to produce β-phenylethanol is carried out in a reactor or a tubular reactor. Since styrene oxide hydrogenation is a strong exothermic reaction, in order to control the heat of reaction, it is often necessary to add a solvent. Solvents are required for the β-phenylethanol preparation process proposed by the patents CN1111169A, U.S. Pat. Nos. 6,979,753, 4,943,667, 2,524,096, etc., which reduces the production efficiency, complicates the product separation process and increases the cost of solvent removal.

In summary, the existing technologies all have certain deficiencies to varying degrees, for example, the problems such as the poor mass transfer effect leads to the need to add auxiliary agents to improve the selectivity, but at the same time, the catalyst life is reduced, the product separation is difficult, and even the product quality is affected; if the catalyst structure and performance are not good, the catalyst is easy to deactivate, the catalyst life is short; if the heat transfer limit of the reactor requires solvent, the separation cost is increased. Therefore, the development of a highly efficient reactor and a highly selective and long-life catalyst are important for improving the preparation method of β-phenylethanol.

SUMMARY OF THE INVENTION

The present invention provides a reaction system for the hydrogenation of styrene oxide to prepare β-phenylethanol; the present invention also provides a catalyst for the hydrogenation of styrene oxide to prepare β-phenylethanol and a preparation method thereof; In the specific embodiments of the present invention, the catalyst has uniform macropores, which can effectively prevent the blockage of catalyst pores and prolong catalyst life. The present invention still further provides a method for the hydrogenation of styrene oxide to prepare β-phenylethanol. In the specific embodiments of the present invention, the method has relatively mild reaction conditions and simple product separation, and is easy to industrialize for scale-up production.

The present invention adopts the following technical solutions:

A reaction system for preparing β-phenylethanol, wherein the reaction system comprises: a micro reaction channel for loading a catalyst, wherein the micro reaction channel is a coiled tube having a microsized diameter and used as reaction site; a Y-shaped channel communicated with one end of the micro reaction channel, wherein the two channels of the Y-shaped channel are respectively one gas channel for introducing a gas reaction raw material and one liquid channel for introducing a liquid reaction raw material; an outlet filtration unit communicated with the other end of the micro reaction channel, wherein the outlet filtration unit is used for preventing the catalyst in the micro reaction channel from passing through and allowing liquid product and gas to flow out; a gas-liquid separation system communicated with the outlet filtration unit, wherein the gas-liquid separation system is used for separating the liquid product from the gas; and an ultrasonic field generator for applying an ultrasonic field to the micro reaction channel.

The reaction system also comprises a preheater(s) for preheating the gas reaction raw material and the liquid reaction raw material and a heater(s) for heating the micro reaction channel.

The ultrasonic field generator has an ultrasonic power of 50-600 W, preferably 150-400 W, more preferably 200-300 W.

The Y-shaped channel has a channel diameter of 5-50 μm, preferably 10-35 μm, more preferably 20-30 μm; the gas channel and the liquid channel of the Y-shaped channel are both composed of a plurality of evenly distributed thin tubes (the thin tube is also called as stream); the number of streams per channel is 1-20, preferably 3-15, more preferably 5-10; preferably, the number and distribution of the thin tubes of the gas channel and the number and distribution of the thin tubes of the liquid channel are exactly the same; the gas reaction raw material and the liquid reaction raw material are respectively divided into a plurality of streams through two channels of the Y-shaped channel and then collected into the micro reaction channel; the micro reaction channel has a diameter of 5-500 μm, preferably 50-350 μm, more preferably 200-300 μm; the outlet filtration unit is filled with an etched silicon column having an average pore diameter of 0.1-15 μm, preferably 0.5-10 μm, more preferably 1-2 μm. Wherein, the etched silicon column is a cylindrical silicon material having a porous structure formed by etching.

In a preferred embodiment, the reaction system can meet the need of adjusting productivity by employing a parallel form.

A catalyst for preparing β-phenylethanol, wherein the catalyst is a nanosized self-assembled catalyst with $Al_2O_3$ as carrier, Ni element and Cu element as active components; wherein, based on the mass of the catalyst, the content of Ni element is 5-30 wt %, preferably 10-27 wt %, more preferably 20-25 wt %; the content of Cu element is 0.5-3.5 wt %, preferably 1-3 wt %, more preferably 1.5-2 wt %; the balance is $Al_2O_3$ carrier.

The catalyst has an average pore diameter of 10-350 nm, preferably 50-300 nm, more preferably 100-150 nm.

The preparation process of the catalyst is:
① Under an uniform stirring condition, mixing 0.001-0.015 mol/L polyisobutylene maleic acid triethanolamine ester and 0.05-0.25 mol/L base oil for lubricating oil fully with a volume ratio of (5-8):1 and raising the temperature slowly to 90-100° C., to obtain mixture A; at the same time, under an uniform stirring condition, mixing 1-5.5 mol/L aqueous solution of urea and 0.5-1.5 mol/L aqueous solution of $Al(NO_3)_3 \cdot 9H_2O$ fully with a volume ratio of 1:(3-5) and heating the mixture to 90-100° C., to obtain mixture B;
② Mixing the mixtures A and B with a mass ratio of 1:1 slowly to form a super solubility micelle, and therefore obtaining a primary super solubility micelle self-assembled body; reacting the primary super solubility micelle self-assembled body at 100-110° C. for 2-4 h, washing the product with water and drying at 150-200° C. for 1-2 h to obtain a secondary nanosized self-assembled body; baking the secondary nanosized self-assembled body at 550-600° C. for 6-8 h and pulverizing to obtain a macroporous $Al_2O_3$ carrier having a particle size of 10-30 μm;
③ Mixing 0.01-0.1 mol/L aqueous solution of $Ni(NO_3)_2$ and 0.01-0.05 mol/L aqueous solution of $Cu(NO_3)_2$ to obtain an immersion liquid; adding the macroporous $Al_2O_3$ carrier powder obtained in step ② to the immersion liquid and mixing them evenly by stirring, to form a fluid slurry;
④ Drying the fluid slurry obtained in step ③ at 110° C.-130° C. for 8-10 h and calcining at 300° C.-500° C. for 3-5 h, which are preferably performed when the fluid slurry is injected into the micro reaction channel of the aforementioned reaction system.

A method for preparing β-phenylethanol, comprising the following steps: (1) heating a reactor loaded with catalyst by introducing pre-heated hydrogen gas; (2) introducing styrene oxide to perform a hydrogenation reaction to obtain β-phenylethanol; the catalyst is a nanosized self-assembled catalyst with $Al_2O_3$ as carrier, Ni element and Cu element as active components or the catalyst is the catalyst obtained by the aforementioned catalyst preparation method, and the reactor used is the aforementioned reaction system.

Also included prior to said step (1) is a reduction step of reducing the catalyst in the reactor.

The reduction step is: firstly raising the temperature of the micro reaction channel to 120-130° C., keeping for 2-2.5 h, then raising the temperature to 200-220° C. and keeping for 18-24 h, to complete the reduction, wherein the hydrogen gas space velocity during the reduction process is 300-500 $h^{-1}$, the pressure is 0.5-1.5 MPa (gauge pressure), and then lowering the temperature to room temperature in hydrogen atmosphere. Wherein, the gauge pressure refers to the portion exceeding atmospheric pressure.

The temperature of the pre-heated hydrogen gas in step (1) is 25-60° C., preferably 30-50° C., more preferably 35-45° C.

In step (2), the styrene oxide is introduced by means of a pump. The flow rate of the hydrogen gas in step (2) is 0.5-13 $Nm^3/h$, preferably 1.5-10 $Nm^3/h$, more preferably 2.5-7 $Nm^3/h$; and the feed rate of styrene oxide is 1-35 Kg/h, preferably 3-20 Kg/h, more preferably 5-10 Kg/h; the molar ratio of hydrogen gas to styrene oxide is 2-69, preferably 2.6-17, more preferably 3.7-14.

In step (2), the reaction temperature is 30-120° C., preferably 40-100° C., more preferably 50-70° C.; the reaction pressure (gauge pressure) is 0.3-10 Mpa, preferably 0.5-3 Mpa, more preferably 1-1.5 Mpa.

The beneficial effects of the specific embodiments of the present invention are:

The β-phenylethanol preparation technique is carried out in the reaction system with an ultrasonic field, and the micro reaction channel has a large specific surface area, which is beneficial to sufficient mass transfer. Another advantage of a large specific surface area lies in that the heat transfer capability is strong, the reaction heat of the hydrogenation of styrene oxide can be removed rapidly, and the reaction is allowed to be carried out under solvent-free conditions, which reduces the process of solvent removal during product refining, simplifies the product separation process, reduces production costs, and meanwhile ensures the genuine flavor of the product; at the same time, the effect of the applied ultrasonic field further enhances the mass transfer, which makes it possible to ensure high selectivity and high yield without adding auxiliary agents in the preparation of β-phenylethanol, and the selectivity of β-phenylethanol can reach 99% or more. The auxiliary agent removal process is reduced, which makes the product separation process simple and the cost low. The extremely large specific surface area of the micro reaction channel, coupled with the mass transfer enhancement of the ultrasonic field, allows the reaction to conduct under mild conditions, reducing equipment input and safety risks. With the reaction system, the equipment has a small floor space and no amplification effect, and multiple reactors can be connected in parallel to flexibly configure the production capacity.

In the specific embodiments of the present invention, a macroporous Ni—Cu/$Al_2O_3$ nanosized self-assembled catalyst is adopted, and the catalyst has a large pore size and uniformity, which can effectively prevent high-boiling substances such as acetals formed during the reaction from blocking the catalyst pores, and at the same time the disturbance provided by the ultrasonic field can further prevent the deposition of high-boiling substances on the catalyst surface, which greatly prolongs the life of the catalyst and reduces the unit consumption of the catalyst; In addition, in the Ni—Cu/$Al_2O_3$ nanosized self-assembled catalyst, the addition of Cu will effectively promote the hydrogenation of phenylacetaldehyde, reduce the probability of phenylacetaldehyde reacting with β-phenylethanol to form high-boiling substances, lower the high-boiling substances content in the reaction solution, reduce the amount of tar and prolong the life of the catalyst.

The ultrasonic field power range selected by the present invention can not only ensure the effect of enhancing the mass transfer, but also will not cause the reactor to vibrate violently. The reasonable combination of the number and diameter of Y-shaped channel and the diameter of the micro reaction channel ensure the mass transfer heat transfer effect, so that the reaction can be carried out without solvent or additives. The preferred catalyst pore size range ensures the life of the catalyst without affecting catalyst strength and selectivity. Reasonable addition amount of Cu can effectively promote the phenylacetaldehyde hydrogenation, reduce the formation of high-boiling substances, prolong the life of the catalyst, and will not affect the reaction rate of main reaction with the ring opening of styrene oxide.

DETAILED DESCRIPTION OF THE INVENTION

The present invention will now be described in the following with reference to specific embodiments. It is to be noted herein that the examples are only used to further illustrate the present invention, and are not to be construed as limiting the protection scope of the present invention. Any non-substantial improvement or adjustment made to the present invention according to its contents shall be included in the protection of the present invention.

The following are the sources of the main raw materials and instruments used in the examples:

Polyisobutylene maleic acid triethanolamine ester: SINOPEC Fushun Research Institute of Petroleum and petrochemicals; Base oil for lubricating oil: South Korea SK Lubricating Oil Company; Urea: Panjin Zhongrun Chemical Co., Ltd.; $Al(NO_3)_3.9H_2O$: Huainan Kedi-chem Technology Co., Ltd.; $Cu(NO_3)_2.3H_2O$: Shanghai Aladdin Bio-chem Technology Co., Ltd.; $Ni(NO_3)_2.6H_2O$: Shanghai Aladdin Bio-chem Technology Co., Ltd.; styrene oxide: Aladdin Industrial Corporation; hydrogen gas: Yantai Wanhua Huasheng Gas Co., Ltd.; sodium hydroxide: Xilong Chemical Co., Ltd.; etched silicon column: Suzhou CSE Semiconductor Equipment Technology Co., Ltd.; ultrasonic field generator: Nanjing Hanzhou Technology Co., Ltd.

The average pore diameter can be measured by nitrogen adsorption-desorption method (BET), and the content of the metal component in the catalyst can be measured by ICP (Ion-Coupling Broad Spectrum Method).

The sample was diluted with HPLC grade ethanol and then subject to GC analysis on SHIMADZU AOC-20i using HP-88 (88%-cyanopropyl-aryl-polysiloxane, 100 m×0.25 mm×0.20 μm) capillary chromatographic column, FID detector. The inlet temperature is 280° C., the detector temperature is 300° C., and the column temperature is controlled by programmed temperature: the initial column temperature is maintained at 50° C. for 0.5 min, and the temperature is raised to 120° C. at 3° C./min for 5 min and the temperature is raised to 220° C. at 20° C./min. The column pressure is 77.3 kpa, the column flow rate is 1.1 ml/min, the split ratio is 1:50, and the injection volume is 0.2 μL. Conversion rate and selectivity were calculated using the area normalization method.

The gas reaction raw material and the liquid reaction raw material are respectively divided into a plurality of streams through the two ends of the Y-shaped channel 1, and then collected into the micro reaction channel 2 loaded with catalyst, and the outlet filtration unit 4 is filled with an etched silicon column for filtering the catalyst and the ultrasonic field generator 3 applies an ultrasonic field to the micro reaction channel.

Figure 5:
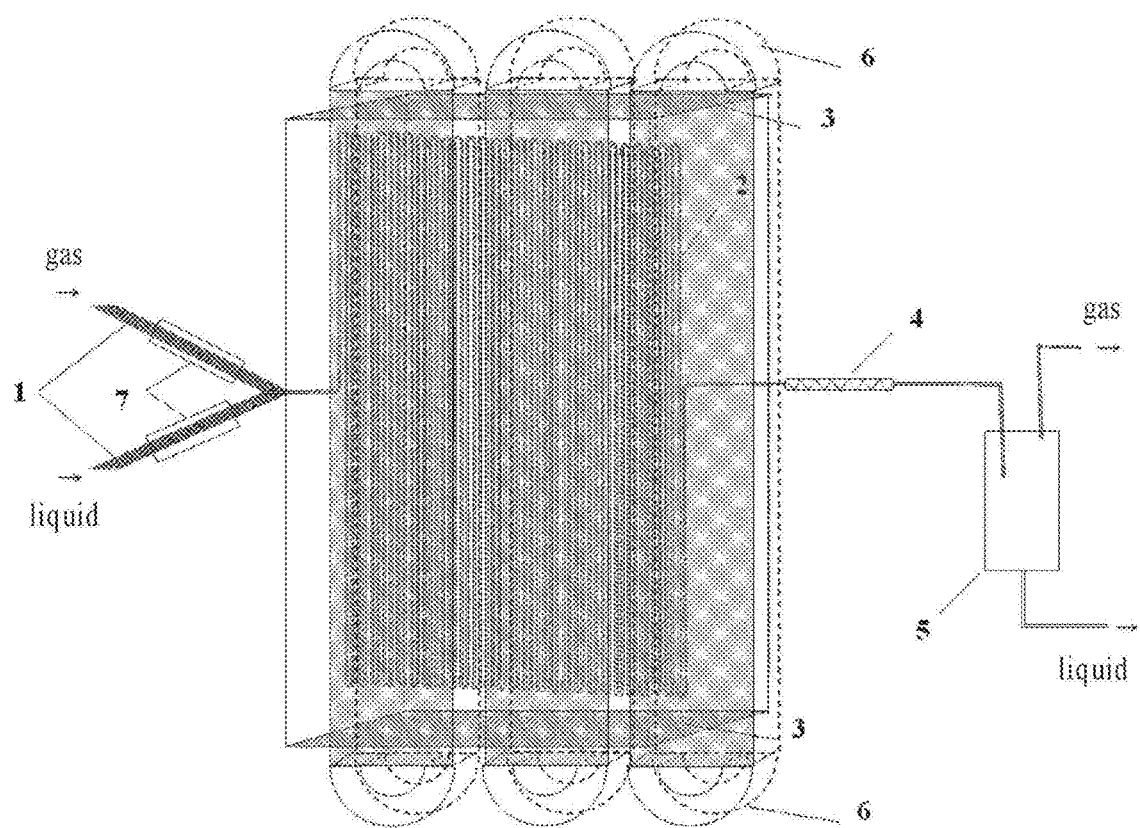
FIG. 5 is a top view of the ultrasonic field micro-packed bed reactor of the present invention, wherein 1 represents: Y-shaped channel, 2 represents: micro reaction channel, 3 represents: ultrasonic field generator, 4 represents: outlet filtration unit, 5 represents: gas-liquid separation system, 6 represents: micro reaction channel heater, 7 represents.

As shown in FIG. 5, the reaction system for preparing β-phenylethanol in the following examples comprises: a micro reaction channel 2, which is a coiled tube having a microsized diameter and used as reaction site; a Y-shaped channel 1 communicated with one end of the micro reaction channel, wherein the two channels of the Y-shaped channel 1 are respectively one gas channel for introducing a gas reaction raw material and one liquid channel for introducing a liquid reaction raw material; an outlet filtration unit 4 communicated with the other end of the micro reaction channel, wherein the outlet filtration unit 4 is used for preventing the catalyst in the micro reaction channel 2 from passing through and allowing liquid product and gas to flow out; a gas-liquid separation system 5 communicated with the outlet filtration unit 4, wherein the gas-liquid separation system 5 is used for separating the liquid product from the gas; an ultrasonic field generator 3 for applying an ultrasonic field to the micro reaction channel 2; a preheater 7 for preheating the gas reaction raw material and the liquid reaction raw material and a heater 6 for heating the micro reaction channel.

Wherein, the ultrasonic field generator 3 is a box, the micro reaction channel 2 is horizontally fixed in the box; the Y-shaped channel 1 and the outlet filtration unit 4 are respectively located outside the box, and respectively located in the middle of the back side and the middle of the front side of the box; the gas channel and the liquid channel of the Y-shaped channel are located at the same height and are disposed in parallel with the bottom surface of the box; the heaters 6 are jacket type heaters and have a total of three sets, the heating elements are placed on the outside of the box by being respectively clamped on the left side and right side of the box, and preheater 7 has two preheaters which are respectively clamped on the gas channel and the liquid channel of the Y-shaped channel.

Figure 6:
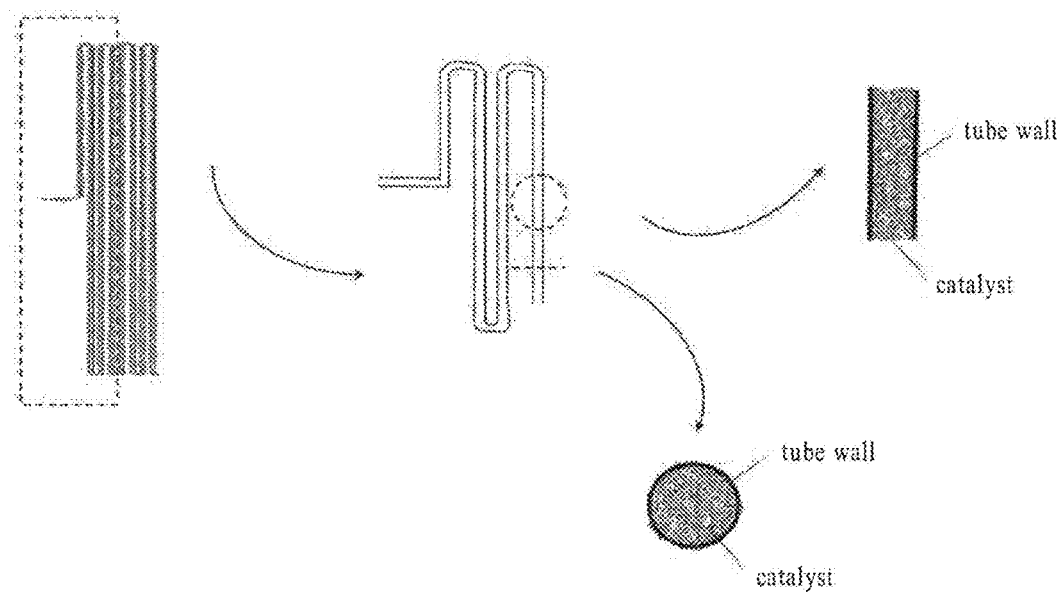
FIG. 6 is a schematic view showing the structure of the micro reaction channel.
Figure 7:
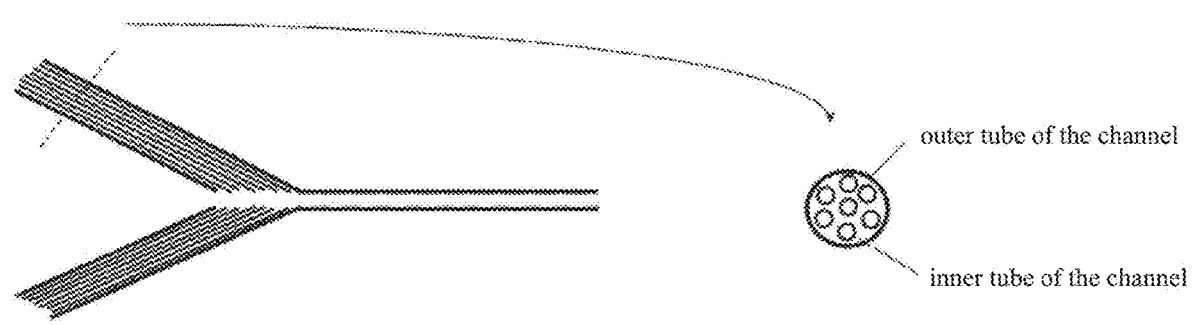
FIG. 7 is a schematic view showing the structure of the Y-shaped channel and a cross-sectional view of the gas channel and liquid channel.

As shown in FIG. 6, the micro reaction channel 2 is a coiled tube; as shown in FIG. 7, the gas channel and the liquid channel of the Y-shaped channel are composed of a plurality of evenly distributed thin tubes, and the number and distribution of the thin tubes of the gas channel and the number and distribution of the thin tubes of the liquid channel are exactly the same.

Some specific parameters of the reaction system, such as ultrasonic power, the diameters of the Y-shaped channel and the micro reaction channel, etc., will be given in the specific examples.

Example 1

Catalyst Preparation:

Ni—Cu/$Al_2O_3$ nanosized self-assembled catalyst CAT-1: based on the mass of the catalyst, the content of Ni was 9.06 wt %, the content of Cu was 1.64 wt %, and the average pore diameter of the catalyst was 33.27 nm.

The Preparation Process of the Catalyst was as Follows:

① Under an uniform stirring condition, 0.008 mol/L polyisobutylene maleic acid triethanolamine ester and 0.15 mol/L base oil for lubricating oil were fully mixed with a volume ratio of 5:1, and the temperature was slowly raised to 100° C., to obtain mixture A; at the same time, 2.5 mol/L aqueous solution of urea and 0.7 mol/L aqueous solution of $Al(NO_3)_3 \cdot 9H_2O$ were fully mixed with a volume ratio of 1:5 and the mixture was heated to 95° C., stirred evenly during this process, to obtain mixture B; then, the mixtures A and B were slowly mixed with a mass ratio of 1:1 to form a super solubility micelle to obtain a primary super solubility micelle self-assembled body; then the primary super solubility micelle self-assembled body was reacted at 105° C. for 3.5 h, the product was washed with water and dried at 200° C. for 2 h to obtain a secondary nanosized self-assembled body, and then the secondary nanosized self-assembled body was baked at 580° C. for 6 h, and pulverized to obtain a macroporous $Al_2O_3$ carrier having an average particle diameter of 13.58 μm.

② 0.02 mol/L aqueous solution of $Ni(NO_3)_2$ and 0.03 mol/L aqueous solution of $Cu(NO_3)_2$ were mixed with a ratio of 9:1 (volume ratio), to obtain an immersion liquid; the macroporous $Al_2O_3$ carrier powder obtained in step ① was added to the immersion liquid and mixed evenly by stirring, to form a fluid slurry.

③ The fluid slurry obtained in step ② was injected into the micro reaction channel 2 of the aforementioned reaction system, and then dried at 125° C. for 8 h and calcined at 350° C. for 5 h under the effect of the heater 6 of the reaction system, to obtain Ni—Cu/$Al_2O_3$ nanosized self-assembled catalyst.

Preparation of β-phenylethanol:

(1) The Ni—Cu/$Al_2O_3$ nanosized self-assembled catalyst in the reaction system (the number of streams per channel of the Y-shaped channel 1 was 8, the diameter of the channel was 17.35 μm, the diameter of the micro reaction channel 2 was 228.86 μm, and the average pore diameter of the silicon column of the outlet filtration unit 4 was 3.52 μm) was reduced in advance: at first hydrogen gas was introduced into the micro reaction channel through the gas channel of the Y-shaped channel, and then the temperature of the micro reaction channel was raised to 125° C. by the heater 6, staying for 2 h, then raised to 220° C., staying for 18 h, to compete the reduction, and then the temperature was lowered to room temperature in hydrogen atmosphere, the hydrogen gas space velocity during the reduction process was 320 $h^{-1}$, and the pressure was 1.5 Mpa (gauge pressure).

(2) After the reduction of the catalyst was completed, the ultrasonic generator was turned on and the ultrasonic power was set to 300 W, and the micro reaction channel was heated by the hydrogen gas which was introduced by the gas channel of the Y-shaped channel and preheated by the preheater 7, wherein the preheating temperature of the hydrogen gas was 35° C.

(3) After the temperature of the micro reaction channel was raised to 35° C., the raw material styrene oxide was fed at a rate of 10 Kg/h for hydrogenation reaction, the flow rate of hydrogen gas was 6.5 $Nm^3$/h, the reaction temperature was controlled to 70° C. and the reaction pressure was 1.5 Mpa. After the reaction was carried out for 8 h, the reaction solution was sampled and the composition of the reaction solution was analyzed, and the results are shown in Table 1.

Example 2

Catalyst Preparation:

Ni—Cu/$Al_2O_3$ nanosized self-assembled catalyst CAT-2: based on the mass of the catalyst, the content of Ni was 17.82 wt %, the content of Cu was 3.17 wt %, and the average pore diameter of the catalyst was 208.69 nm.

The Preparation Process of the Catalyst was as Follows:

① Under an uniform stirring condition, 0.003 mol/L polyisobutylene maleic acid triethanolamine ester and 0.24 mol/L base oil for lubricating oil were fully mixed with a volume ratio of 7:1, and the temperature was slowly raised to 100° C., to obtain mixture A; at the same time, 5.2 mol/L aqueous solution of urea and 1.1 mol/L aqueous solution of $Al(NO_3)_3 \cdot 9H_2O$ were fully mixed with a volume ratio of 1:3.3 and the mixture was heated to 90° C., stirred evenly during this process, to obtain mixture B; then, the mixtures A and B were slowly mixed with a mass ratio of 1:1 to form a super solubility micelle to obtain a primary super solubility micelle self-assembled body; the primary super solubility micelle self-assembled body was reacted at 105° C. for 3 h, the product was washed with water and dried at 185° C. for 1.5 h to obtain a secondary nanosized self-assembled body, and then the secondary nanosized self-assembled body was baked at 550° C. for 8 h, and pulverized to obtain a macro porous $Al_2O_3$ carrier having an average particle diameter of 19.36 μm.

② 0.034 mol/L aqueous solution of Ni(NO$_3$)$_2$ and 0.05 mol/L aqueous solution of Cu(NO$_3$)$_2$ were mixed with a ratio of 9:1 (volume ratio), to obtain an immersion liquid; the macro porous Al$_2$O$_3$ carrier powder obtained in step ① was added to the immersion liquid and mixed evenly by stirring, to form a fluid slurry.

③ The fluid slurry obtained in step ② was injected into the micro reaction channel 2 of the aforementioned reaction system, and then dried at 110° C. for 8 h and calcined at 500° C. for 5 h under the effect of the heater 6 of the reaction system, to obtain Ni—Cu/Al$_2$O$_3$ nanosized self-assembled catalyst.

Preparation of β-phenylethanol:

(1) The Ni—Cu/Al$_2$O$_3$ nanosized self-assembled catalyst in the reaction system (the number of streams per channel of the Y-shaped channel 1 was 14, the diameter of the channel was 25.56 μm, the diameter of the micro reaction channel 2 was 342.87 μm, and the average pore diameter of the silicon column of the outlet filtration unit 4 was 1.63 μm) was reduced in advance: at first hydrogen gas was introduced into the micro reaction channel through the gas channel of the Y-shaped channel, and then the temperature of the micro reaction channel was raised to 120° C. by the heater 6, staying for 2.5 h, then raised to 200° C., staying for 18 h to complete the reduction, and then the temperature was lowered to room temperature in hydrogen atmosphere, the hydrogen gas space velocity during the reduction process was 500 h$^{-1}$, and the pressure was 0.5 Mpa (gauge pressure).

(2) After the reduction of the catalyst was completed, the ultrasonic generator was turned on and the ultrasonic power was set to 200 W, and the micro reaction channel was heated by the hydrogen gas which was introduced by the gas channel of the Y-shaped channel and pre-heated by the preheater 7, wherein the preheating temperature of the hydrogen gas was 40° C.

(3) After the temperature of the micro reaction channel was raised to 40° C., the raw material styrene oxide was fed at a rate of 5 Kg/h for hydrogenation reaction, the flow rate of hydrogen gas was 2 Nm$^3$/h, the reaction temperature was controlled to 50° C. and the reaction pressure was 0.5 Mpa. After the reaction was carried out for 8 h, the reaction solution was sampled and the composition of the reaction solution was analyzed, and the results are shown in Table 1.

Example 3

Catalyst Preparation:

Ni—Cu/Al$_2$O$_3$ nanosized self-assembled catalyst CAT-3: based on the mass of the catalyst, the content of Ni was 24.88 wt %, the content of Cu was 1.36 wt %, and the average pore diameter of the catalyst was 146.21 nm.

The Preparation Process of the Catalyst was as Follows:

① Under an uniform stirring condition, 0.015 mol/L polyisobutylene maleic acid triethanolamine ester and 0.06 mol/L base oil for lubricating oil were fully mixed with a volume ratio of 7:1, and the temperature was slowly raised to 95° C., to obtain mixture A; at the same time, 2.6 mol/L aqueous solution of urea and 0.75 mol/L aqueous solution of Al(NO$_3$)$_3$.9H$_2$O were fully mixed with a volume ratio of 1:4.7 and the mixture was heated to 100° C., stirred evenly during this process, to obtain mixture B; then, the mixtures A and B were slowly mixed with a mass ratio of 1:1 to form a super solubility micelle to obtain a primary super solubility micelle self-assembled body; then the primary super solubility micelle self-assembled body was reacted at 110° C. for 2 h, the product was washed with water and dried at 150° C. for 2 h to obtain a secondary nanosized self-assembled body, and then the secondary nanosized self-assembled body was baked at 600° C. for 6 h, and pulverized to obtain a macro porous Al$_2$O$_3$ carrier having an average particle diameter of 28.36 μm.

② 0.044 mol/L aqueous solution of Ni(NO$_3$)$_2$ and 0.02 mol/L aqueous solution of Cu(NO$_3$)$_2$ were mixed with a ratio of 9:1 (volume ratio), to obtain an immersion liquid; the macroporous Al$_2$O$_3$ carrier powder obtained in step ① was added to the immersion liquid, to form a fluid slurry.

③ The fluid slurry obtained in step ② was injected into the micro reaction channel 2 of the aforementioned reaction system, and then dried at 130° C. for 9 h and calcined at 450° C. for 5 h under the effect of the heater 6 of the reaction system, to obtain Ni—Cu/Al$_2$O$_3$ nanosized self-assembled catalyst.

Preparation of β-phenylethanol:

(1) The Ni—Cu/Al$_2$O$_3$ nanosized self-assembled catalyst in the reaction system (the number of streams per channel of the Y-shaped channel 1 was 17, the diameter of the channel was 7.32 μm, the diameter of the micro reaction channel 2 was 48.62 μm, and the average pore diameter of the silicon column of the outlet filtration unit 4 was 11.33 μm) was reduced in advance: at first hydrogen gas was introduced into the micro reaction channel through the gas channel of the Y-shaped channel, and then the temperature of the micro reaction channel was raised to 125° C. by the heater 6, staying for 2.5 h, then raised to 210° C., staying for 22 h to complete the reduction, and then the temperature was lowered to room temperature in hydrogen atmosphere, the hydrogen gas space velocity during the reduction process was 450 h$^{-1}$, and the pressure was 1.0 Mpa (gauge pressure).

(2) After the reduction of the catalyst was completed, the ultrasonic generator was turned on and the ultrasonic power was set to 250 W, and the reactor was heated by the hydrogen gas which was introduced by the gas channel of the Y-shaped channel and pre-heated by the preheater 7, wherein the preheating temperature of the hydrogen gas was 25° C.

(3) After the temperature of the micro reaction channel was raised to 25° C., the raw material styrene oxide was fed at a rate of 7.5 Kg/h for hydrogenation reaction, the flow rate of hydrogen gas was 4.5 Nm$^3$/h, the reaction temperature was controlled to 35° C. and the reaction pressure was 7 Mpa. After the reaction was carried out for 8 h, the reaction solution was sampled and the composition of the reaction solution was analyzed, and the results are shown in Table 1.

Example 4

Catalyst Preparation:

Ni—Cu/Al$_2$O$_3$ nanosized self-assembled catalyst CAT-4: based on the mass of the catalyst, the content of Ni was 22.37 wt %, the content of Cu was 1.71 wt %, and the average pore diameter of the catalyst was 311.58 nm.

The Preparation Process of the Catalyst was as Follows:

① Under an uniform stirring condition, 0.002 mol/L polyisobutylene maleic acid triethanolamine ester and 0.22 mol/L base oil for lubricating oil were fully mixed with a volume ratio of 8:1, and the temperature was slowly raised to 95° C., to obtain mixture A; at the same time, 1.1 mol/L aqueous solution of urea and 1.35 mol/L aqueous solution of Al(NO$_3$)$_3$.9H$_2$O were fully mixed with a volume ratio of 1:3.5 and the mixture was heated to 100° C., stirred evenly during this process, to obtain mixture B; then, the mixtures A and B were slowly mixed with a mass ratio of 1:1 to form a super solubility micelle to obtain a primary super solubility micelle self-assembled body; then the primary super solubility micelle self-assembled body was reacted at 110° C. for 4 h, the product was washed with water and dried at 200° C. for 1.5 h to obtain a secondary nanosized self-assembled body, and then the secondary nanosized self-assembled body was baked at 560° C. for 7.5 h, and pulverized to obtain a macroporous $Al_2O_3$ carrier having an average particle diameter of 19.64 μm.

② 0.047 mol/L aqueous solution of $Ni(NO_3)_2$ and 0.03 mol/L aqueous solution of $Cu(NO_3)_2$ were mixed with a ratio of 9:1 (volume ratio), to obtain an immersion liquid; the macroporous $Al_2O_3$ carrier powder obtained in step ① was added to the immersion liquid, to form a fluid slurry.

③ The fluid slurry obtained in step ② was injected into the micro reaction channel 2 of the aforementioned reaction system, and then dried at 118° C. for 10 h and calcined at 500° C. for 5 h under the effect of the heater 6 of the reaction system, to obtain Ni—Cu/$Al_2O_3$ nanosized self-assembled catalyst.

Preparation of β-phenylethanol:

(1) The Ni—Cu/$Al_2O_3$ nanosized self-assembled catalyst in the reaction system (the number of streams per channel of the Y-shaped channel 1 was 8, the diameter of the channel was 15.98 μm, the diameter of the micro reaction channel 2 was 256.76 μm, and the average pore diameter of the silicon column of the outlet filtration unit 4 was 8.52 μm) was reduced in advance: at first hydrogen gas was introduced into the micro reaction channel through the gas channel of the Y-shaped channel, and then the temperature of the micro reaction channel was raised to 120° C. by the heater 6, staying for 2.5 h, then raised to 220° C., staying for 20 h to complete the reduction, and then the temperature was lowered to room temperature in hydrogen atmosphere, the hydrogen gas space velocity during the reduction process was 400 $h^{-1}$, and the pressure was 0.8 Mpa (gauge pressure).

(2) After the reduction of the catalyst was completed, the ultrasonic generator was turned on and the ultrasonic power was set to 400 W, and the micro reaction channel was heated by the hydrogen gas which was introduced by the gas channel of the Y-shaped channel and pre-heated by the preheater 7, wherein the preheating temperature of the hydrogen gas was 40° C.

(3) After the temperature of the micro reaction channel was raised to 40° C., the raw material styrene oxide was fed at a rate of 5 Kg/h for hydrogenation reaction, the flow rate of hydrogen gas was 3 $Nm^3/h$, the reaction temperature was controlled to 65° C. and the reaction pressure was 0.8 Mpa. After the reaction was carried out for 8 h, the reaction solution was sampled and the composition of the reaction solution was analyzed, and the results are shown in Table 1.

Example 5

Catalyst Preparation:

Ni—Cu/$Al_2O_3$ nanosized self-assembled catalyst CAT-5: based on the mass of the catalyst, the content of Ni was 23.09 wt %, the content of Cu was 1.82 wt %, and the average pore diameter of the catalyst was 136.59 nm.

The Preparation Process of the Catalyst was:

① Under an uniform stirring condition, 0.003 mol/L polyisobutylene maleic acid triethanolamine ester and 0.24 mol/L base oil for lubricating oil were fully mixed with a volume ratio of 8:1, and the temperature was slowly raised to 95° C., to obtain mixture A; at the same time, 3.5 mol/L aqueous solution of urea and 1.35 mol/L aqueous solution of $Al(NO_3)_3 \cdot 9H_2O$ were fully mixed with a volume ratio of 1:4 and the mixture was heated to 100° C., stirred evenly during this process, to obtain mixture B; then, the mixtures A and B were slowly mixed with a mass ratio of 1:1 to form a super solubility micelle to obtain a primary super solubility micelle self-assembled body; then the primary super solubility micelle self-assembled body was reacted at 110° C. for 3 h, the product was washed with water and dried at 180° C. for 2 h to obtain a secondary nanosized self-assembled body, and then the secondary nanosized self-assembled body was baked at 600° C. for 7 h, and pulverized to obtain a macroporous $Al_2O_3$ carrier having an average particle diameter of 25.71 μm.

② 0.054 mol/L aqueous solution of $Ni(NO_3)_2$ and 0.035 mol/L aqueous solution of $Cu(NO_3)_2$ were mixed with a ratio of 9:1 (volume ratio), to obtain an immersion liquid; the macroporous $Al_2O_3$ carrier powder obtained in step ① was added to the immersion liquid, to form a fluid slurry.

③ The fluid slurry obtained in step ② was injected into the micro reaction channel 2 of the aforementioned reaction system, and then dried at 125° C. for 9 h and calcined at 500° C. for 4 h under the effect of the heater 6 of the reaction system, to obtain Ni—Cu/$Al_2O_3$ nanosized self-assembled catalyst.

Preparation of β-phenylethanol:

(1) The Ni—Cu/$Al_2O_3$ nanosized self-assembled catalyst in the reaction system (the number of streams per channel of the Y-shaped channel 1 was 10, the diameter of the channel was 45.85 μm, the diameter of the micro reaction channel 2 was 208.61 μm, and the average pore diameter of the silicon column of the outlet filtration unit 4 was 1.53 μm) was reduced in advance: at first hydrogen gas was introduced into the micro reaction channel through the gas channel of the Y-shaped channel, and then the temperature of the micro reaction channel was raised to 130° C. by the heater 6, staying for 2.5 h, then raised to 220° C., staying for 24 h to complete the reduction, and then the temperature was lowered to room temperature in hydrogen atmosphere, the hydrogen gas space velocity during the reduction process is 450 $h^{-1}$, the pressure is 1.5 Mpa (gauge pressure).

(2) After the reduction of the catalyst was completed, the ultrasonic generator was turned on and the ultrasonic power was set to 350 W, and the micro reaction channel was heated by the hydrogen gas which was introduced by the gas channel of the Y-shaped channel and pre-heated by the preheater 7, wherein the preheating temperature of the hydrogen gas was 45° C.

(3) After the temperature of the micro reaction channel was raised to 45° C., the raw material styrene oxide was fed at a rate of 7.5 Kg/h for hydrogenation reaction, the flow rate of hydrogen gas was 6 $Nm^3/h$, the reaction temperature was controlled to 110° C. and the reaction pressure was 1.0 Mpa. After the reaction was carried out for 8 h, the reaction solution was sampled and the composition of the reaction solution was analyzed at intervals. The catalyst performance change during the long-term operation was investigated, and the total operation was 4500 h, and the results are shown in Table 1.

As can be seen from the figure, under the process conditions of the present invention, the catalyst had a stable performance, long life and high product selectivity.

Comparative Example 1

10 g Raney6800 catalyst (Grace), 50 g styrene oxide and 450 g ethanol were added to a reactor (model GSH-1, material 316L, the manufacturer is Weihai Chemical Machinery Co., Ltd.), and after the reactor was closed to replace the air while the pressure was maintained, hydrogen gas was introduced to perform the reaction, wherein the reaction temperature was 80° C., the reaction pressure was 6 Mpa, the stirring speed was 700 rpm and the reaction time was 3 h. After the reaction was completed, the reaction solution was sampled and analyzed, and the results are shown in Table 1.

Comparative Example 2

10 g Raney6800 catalyst (Grace), 50 g styrene oxide, 450 g ethanol and 0.2 g NaOH were added to a reactor (model GSH-1, material 316L, the manufacturer is Weihai Chemical Machinery Co., Ltd.), and after the reactor was closed to replace the air while the pressure was maintained, hydrogen gas was introduced to perform the reaction, wherein the reaction temperature was 60° C., the reaction pressure was 1 Mpa, the stirring speed was 700 rpm, and the reaction time was 3 h. After the reaction was completed, the reaction solution was sampled and analyzed, and the results are shown in Table 1. As can be seen from the table, the selectivity of β-phenylethanol is not ideal even under the condition of adding auxiliary agent NaOH, and the addition of the auxiliary agent will cause the bottom of the fractionating tower to be blocked during the separation process, and meanwhile will affect the product quality.

Comparative Example 3

30 g Raney6800 catalyst (Grace) and 500 g styrene oxide were added to a reactor (model GSH-1, material 316L, the manufacturer is Weihai Chemical Machinery Co., Ltd.), and after the reactor was closed to replace the air while the pressure was maintained and exchanged, hydrogen gas was introduced to perform the reaction, wherein the reaction temperature was 80° C., the reaction pressure was 6 MPa, the stirring speed was 700 rpm, and the reaction time was 4.5 h. After the reaction was completed, the reaction solution was sampled and analyzed, and the results are shown in Table 1.

Comparative Example 4

Figure 1:
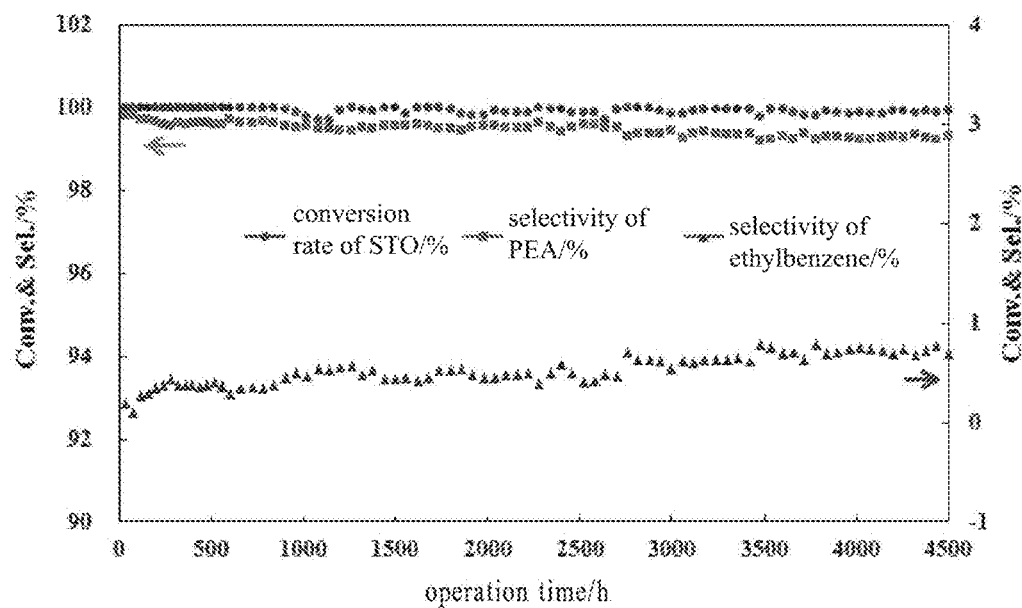
FIG. 1 shows the reaction results of Example 5.
Figure 2:
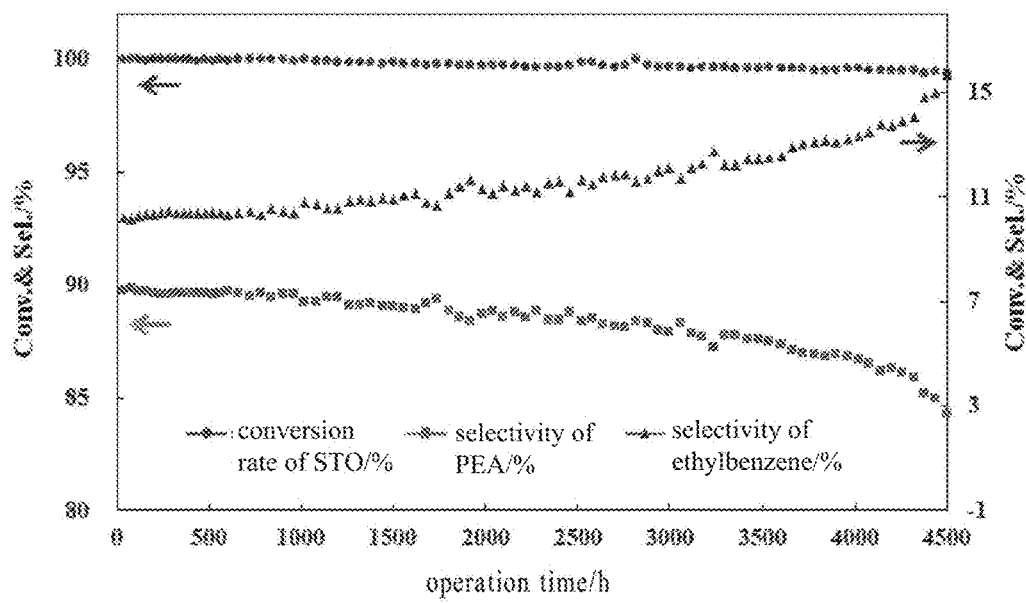
FIG. 2 shows the reaction results of Comparative example 4.

The hydrogenation reaction of styrene oxide was carried out in a common fixed bed with a diameter of 20 mm (model TORCH, material 316SS, manufacturer is Beijing Tuochuan Petrochemical Evaluation Device Technology Development Co., Ltd., reaction tube length is 1400 mm), wherein the catalyst, catalyst reduction procedure, reaction temperature, pressure and space velocity were all the same as that in Example 5, and the operation was continued for 4500 h. The reaction results are shown in FIG. 2.

As can be seen from the figure, with the common fixed bed reactor, the reaction effect was significantly worse than that of the ultrasonic micro-packed bed reactor, and the selectivity of the product β-phenylethanol was obviously decreased.

Comparative Example 5

Figure 3:
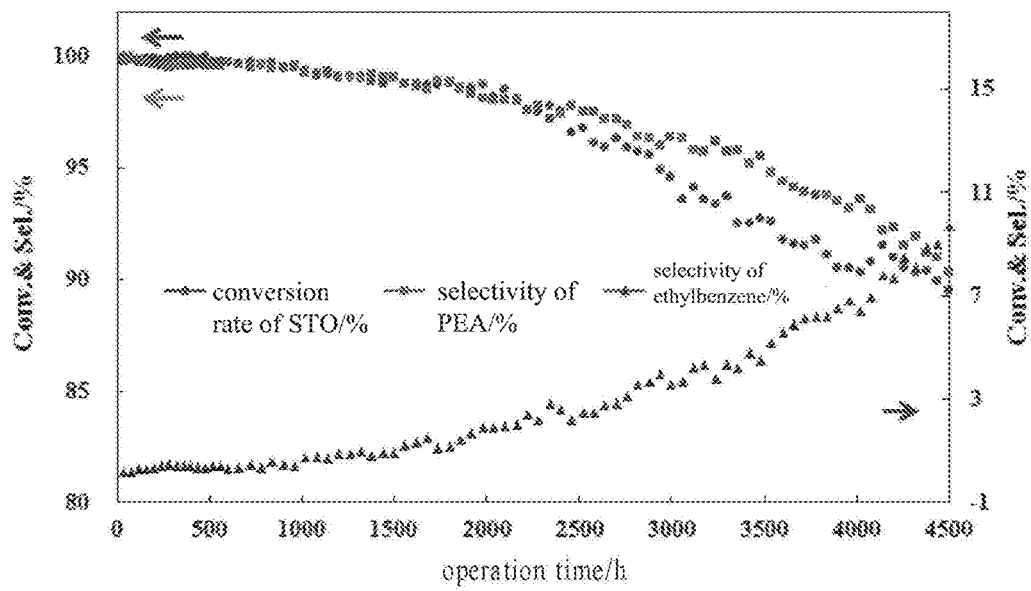
FIG. 3 shows the reaction results of Comparative example 5.

The Ni—Cu/Al$_2$O$_3$ nanosized self-assembled catalyst in Example 5 was replaced with Raney 6800 (Grace), and the other process parameters were all the same as that in Example 5, and the operation was continued for 4500 h. The reaction results are shown in FIG. 3.

As can be seen from the figure, the performance of the catalyst Raney 6800 was significantly inferior to that of the Ni—Cu/Al$_2$O$_3$ nanosized self-assembled catalyst described in this patent.

Comparative Example 6

Figure 4:
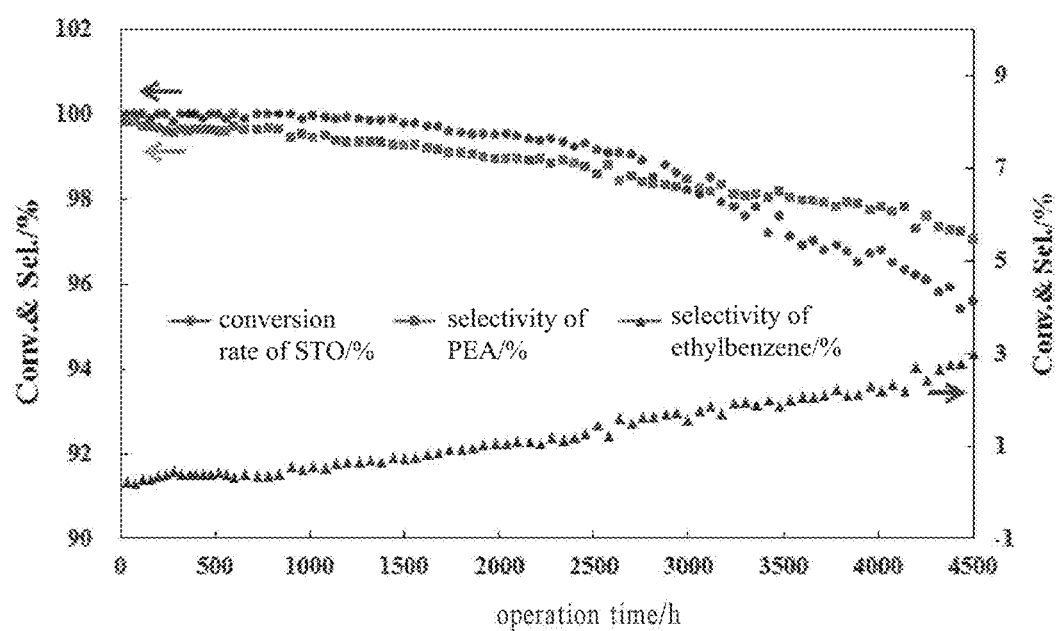
FIG. 4 shows the reaction results of Comparative example 6.

The styrene oxide was hydrogenated without ultrasonic field and the other process parameters were all the same as that in Example 5, and the operation was continued for 4500 h. The reaction results are shown in FIG. 4.

As can be seen from the figure, after the ultrasonic field was removed, the reaction effect was significantly deteriorated and the catalyst stability was lowered.

TABLE 1

| No. | Conversion rate of styrene oxide/% | Selectivity of β-phenyl-ethanol/% | Selectivity of ethyl-benzene/% |
|---|---|---|---|
| Example 1 | 100 | 99.34 | 0.51 |
| Example 2 | 100 | 99.07 | 0.73 |
| Example 3 | 100 | 99.52 | 0.36 |
| Example 4 | 100 | 99.35 | 0.48 |
| Comparative example 1 | 100 | 91.42 | 8.05 |
| Comparative example 2 | 100 | 98.57 | 1.26 |
| Comparative example 3 | 100 | 79.67 | 20.15 |

The invention claimed is:

1. A reaction system for preparing β-phenylethanol, wherein the reaction system comprises:
a micro reaction channel for loading a catalyst, wherein the micro reaction channel is a coiled tube having a microsized diameter and used as a reaction site;
a Y-shaped channel communicated with one end of the micro reaction channel, the Y-shaped channel comprising two channels, wherein the two channels of the Y-shaped channel are respectively one gas channel for introducing a gas reaction raw material and one liquid channel for introducing a liquid reaction raw material;
an outlet filtration unit communicated with the other end of the micro reaction channel, wherein the outlet filtration unit is used for preventing the catalyst in the micro reaction channel from passing through and allowing liquid product and gas to flow out;
a gas-liquid separation system communicated with the outlet filtration unit, wherein the gas-liquid separation system is used for separating the liquid product from the gas; and
an ultrasonic field generator for applying an ultrasonic field to the micro reaction channel.

2. The reaction system according to claim 1, wherein the ultrasonic field generator has an ultrasonic power of 50-600 W.

3. The reaction system according to claim 1, wherein the Y-shaped channel has at least one channel with a channel diameter of 5-50 μm; the gas channel and the liquid channel of the Y-shaped channel are both composed of a plurality of evenly distributed thin tubes; the number of the thin tubes per channel is 1-20; the number and distribution of the thin tubes of the gas channel and the number and distribution of the thin tubes of the liquid channel are the same; the micro reaction channel has a diameter of 5-500 μm; the outlet filtration unit is an etched silicon column having an average pore diameter of 0.1-15 μm.

4. A catalyst for preparing β-phenylethanol, wherein the catalyst is a nanosized self-assembled catalyst with Al$_2$O$_3$ as a carrier, Ni element and Cu element as active components; wherein, based on the mass of the catalyst, the content of the Ni element is 5-30 wt %; the content of the Cu element is 0.5-3.5 wt %; the balance is $Al_2O_3$ carrier.

5. The catalyst according to claim 4, wherein the catalyst has an average pore diameter of 10-350 nm.

6. The catalyst according to claim 4, wherein the catalyst is obtained by the preparation method comprising the following steps:
① under an uniform stirring condition, mixing 0.001-0.015 mol/L polyisobutylene maleic acid triethanolamine ester and 0.05-0.25 mol/L base oil for lubricating oil fully with a volume ratio of (5-8):1 and raising the temperature slowly to 90-100° C. to obtain mixture A; under an uniform stirring condition, mixing 1-5.5 mol/L aqueous solution of urea and 0.5-1.5 mol/L aqueous solution of $Al(NO_3)_3.9H_2O$ with a volume ratio of 1:(3-5) and heating the mixture to 90-100° C. to obtain mixture B;
② mixing the mixtures A and B with a mass ratio of 1:1 to form a super solubility micelle to obtain a primary super solubility micelle self-assembled body; reacting the primary super solubility micelle self-assembled body at 100-110° C., washing the product with water and drying to obtain a secondary nanosized self-assembled body; baking and pulverizing the secondary nanosized self-assembled body to obtain $Al_2O_3$ carrier;
③ mixing 0.01-0.1 mol/L aqueous solution of $Ni(NO_3)_2$ and 0.01-0.05 mol/L aqueous solution of $Cu(NO_3)_2$ to obtain an immersion liquid; adding the $Al_2O_3$ carrier powder obtained in step ② to the immersion liquid and mixing them evenly by stirring to form a fluid slurry;
④ drying and calcining the fluid slurry obtained in step ③ to obtain the catalyst.

7. The catalyst according to claim 6, wherein in step ②, the reaction time of the primary super solubility micelle self-assembled body is 2-4 h, the drying temperature of the primary super solubility micelle self-assembled body is 150-200° C., the calcination temperature of the secondary nanosized self-assembled body is 550-600° C., the calcination time of the secondary nanosized self-assembled body is 6-8 h, and the particle diameter of the pulverized $Al_2O_3$ carrier is 10-30 μm; in step ④, the drying temperature is 110-130° C., the drying time is 8-10 h, the calcination temperature is 300° C.-500° C., and the calcination time is 3-5 h; in step ④, the calcination is performed by injecting the fluid slurry obtained in step ③ into the micro reaction channel of the reaction system according to claim 1.

8. A method for preparing β-phenylethanol, comprising the following steps:
(1) heating a reactor loaded with catalyst by introducing pre-heated hydrogen gas;
(2) introducing styrene oxide to perform a hydrogenation reaction to obtain β-phenylethanol;
wherein, the catalyst is the catalyst according to claim 4, the reactor used is the reaction system according to claim 1.

9. The method according to claim 8, wherein prior to step (1), the method comprises a step of reducing the catalyst in the reactor.

10. The method according to claim 9, wherein the reduction step is: firstly raising the temperature of the micro reaction channel to 120-130° C., keeping for 2-2.5 h, then raising the temperature to 200-220° C., and keeping for 18-24 h, to complete the reduction, wherein the hydrogen gas space velocity during the reduction is 300-500 $h^{-1}$, the pressure is 0.5-1.5 MPa, and then lowering the temperature to room temperature in hydrogen atmosphere.

11. The method according to claim 8, wherein the temperature of the pre-heated hydrogen gas in step (1) is 25-60° C.

12. The method according to claim 8, wherein in step (2), the flow rate of hydrogen gas is 0.5-13 $Nm^3/h$; the feed rate of styrene oxide is 1-35 Kg/h; the molar ratio of hydrogen gas to styrene oxide is 2-69.

13. The method according to claim 8, wherein in step (2), the reaction temperature is 30-120° C.; the reaction pressure is 0.3-10 Mpa.

14. The reaction system according to claim 2, wherein the Y-shaped channel has at least one channel having a channel diameter of 5-50 μm; the gas channel and the liquid channel of the Y-shaped channel are both composed of a plurality of evenly distributed thin tubes; the number of the thin tubes per channel is 1-20; the number and distribution of the thin tubes of the gas channel and the number and distribution of the thin tubes of the liquid channel are exactly the same; the micro reaction channel has a diameter of 5-500 μm; the outlet filtration unit is an etched silicon column having an average pore diameter of 0.1-15 μm.

15. The method according to claim 9, wherein the temperature of the pre-heated hydrogen gas in step (1) is 25-60° C.

16. The method according to claim 10, wherein the temperature of the pre-heated hydrogen gas in step (1) is 25-60° C.

17. The method according to claim 9, wherein in step (2), the flow rate of hydrogen gas is 0.5-13 $Nm^3/h$; the feed rate of styrene oxide is 1-35 Kg/h; the molar ratio of hydrogen gas to styrene oxide is 2-69.

18. The method according to claim 10, wherein in step (2), the flow rate of hydrogen gas is 0.5-13 $Nm^3/h$; the feed rate of styrene oxide is 1-35 Kg/h; the molar ratio of hydrogen gas to styrene oxide is 2-69.

19. The method according to claim 11, wherein in step (2), the flow rate of hydrogen gas is 0.5-13 $Nm^3/h$; the feed rate of styrene oxide is 1-35 Kg/h; the molar ratio of hydrogen gas to styrene oxide is 2-69.

20. The method according to claim 9, wherein in step (2), the reaction temperature is 30-120° C.; the reaction pressure is 0.3-10 Mpa.

\* \* \* \* \*